United States Patent [19]
Cotarca et al.

[11] Patent Number: 5,872,267
[45] Date of Patent: Feb. 16, 1999

[54] PROCESS FOR PRODUCING AN OMEGA-FUNCTIONALIZED ALIPHATIC CARBOXYLIC ACID AND INTERMEDIATE PRODUCTS OF SAID PROCESS

[75] Inventors: Livius Cotarca, Cervignano del Friuli; Paolo Maggioni, Montevecchia; Alfonso Nardelli, Cervignano del Friuli, all of Italy

[73] Assignee: Industrie Chimiche Caffaro, S.p.A., Italy

[21] Appl. No.: 556,991

[22] PCT Filed: Jun. 8, 1994

[86] PCT No.: PCT/EP94/01865

§ 371 Date: Apr. 16, 1996

§ 102(e) Date: Apr. 16, 1996

[87] PCT Pub. No.: WO94/29257

PCT Pub. Date: Dec. 22, 1994

[30] Foreign Application Priority Data

Jun. 15, 1993 [IT] Italy .................. MI93A1273

[51] Int. Cl.$^6$ .................................................. C07C 51/16
[52] U.S. Cl. .................. 554/132; 584/134; 584/135; 584/138; 584/141
[58] Field of Search .................. 584/115, 132, 584/134, 135, 138, 141

[56] References Cited

U.S. PATENT DOCUMENTS 4,322,547  3/1982  Minisci et al. .

OTHER PUBLICATIONS

Burns, et al., *Highly Reactive Magnesium and its Application to Organic Synthesis*, J. of Organic Chemistry, 52(16):3674, 1987.

Zakharkin, et al., Abstract No. 21911 g: 2E–Dodecendioic) *Acid from Dodecandioic Acid*, Chemical Abstracts, 99(3):569, 1983.

*Primary Examiner*—Paul J. Killos
*Assistant Examiner*—Deborah D. Carr
*Attorney, Agent, or Firm*—Henry D. Coleman; R. Neil Sudol

[57] ABSTRACT

A process for producing an omega-functionalized aliphatic carboxylic acid starting from cyclohexanone and omega-functionalized α-olefins. The process comprises an addition step, an oxidation step, an isomerization step, one or more hydrogenation steps and hydrolysis. The process allows to use raw materials that are available at low cost and to achieve high selectivity and high yield with industrially simple steps. The process includes the production of new intermediate products.

27 Claims, No Drawings

PROCESS FOR PRODUCING AN OMEGA-FUNCTIONALIZED ALIPHATIC CARBOXYLIC ACID AND INTERMEDIATE PRODUCTS OF SAID PROCESS

This application is a 371 of PCT/EP94/01865 filed Jun. 8, 1994.

The present invention relates to a process for producing an omega-functionalized aliphatic carboxylic acid that has over 7 carbon atoms and to the intermediate products of this process.

More particularly, the present invention relates to the production of aliphatic carboxylic acids that have more than 7 carbon atoms and can be used in the production of polyamides with a large number of carbon atoms, even more particularly polyamides with 9 carbon atoms (nylon 9 and nylon 6,9). These polyamides are particularly appreciated due to their mechanical and elastic characteristics. Despite this, current worldwide industrial production of polyamide 9 is practically nonexistent due to lack of an industrially feasible process for producing 9 amino nonanoic acid with the required degree of purity.

The present invention furthermore relates particularly to the production of 1,9-nonandioic acid (azelaic acid), which is used in the field of lubricants, polyester and alkyd resins, as plasticizer and as a drug for dermatological use, and in the production of polyamide 6,9.

A process for oxidizing ketones, including cyclic ketones, by using permonosulfuric acid as an oxidizing agent has been known since the last century as the Baeyer-Villiger reaction (A. Von Baeyer and V. Villiger, Ber. 1899, 32, 3265; 1400, 33, 858). Other oxidizing agents have been used for this reaction, such as for example: peracetic acid, described by R. Criegel (Liebig Annalen, 1948, 560, 127) and in UK patent No. 1,203,752, peracid salts such as magnesium permonophthalate described in Syntesis 1015–1017, 1987, or persalts such as sodium perborate, described in U.S. Pat. No. 4,988,825, whereas the agent used most is m-chloroperbenzoic acid. More recently, methods have been described for synthesizing lactones from ketones, using molecular oxygen in the presence of catalysts, Tetrahedron Lett. 33,75557–60, 1992. In general, the synthesis of lactones starting from cyclic ketones has unpredictable regioselectivity and chemoselectivity.

Processes for producing polyamides 9 are known and are described by K. A. Pollart and R. E. Miller, (J. Am. Chem. Soc., 27, 2392, 1962), by William R. Miller et al. (Ind. Eng. Chem. Prod. Res. Develop., Vol 10, No. 4, 1971) and by R. B. Perkins, Jr. et al. (Journal of the American Oil Chemists' Society, Vol 52, November 1975); processes for producing azelaic acid are also known and described in Ullmann's Encyclopedia of Industrial Chemistry, fifth edition, volume A 8, pages 523–539, and in the Kirk-Othmer Enc., Vol. 7, page 623. These known processes are all based on a complex process for the ozonolysis of fatty acids of natural origin such as oleic acid or soya oil. The ozonolysis step is delicate and intrinsically dangerous and produces, at the end of the process, a mixture of unsaturated products that are very difficult to purify and for which purification is in any case industrially possible only up to 80–90%. Furthermore, the availability and characteristics of the initial starting products fluctuate. Finally, it is unavoidable to also obtain additional co-products. For example, starting from oleic acid one obtains azelaic acid but also, unavoidably, pelargonic acid, with severe limitations to the free use of the individual products.

A process for synthesizing 9 amino nonanoic acid, starting from sabacic acid by means of a monoesterification, ammonolysis and Hofmann degradation has been described (W. Baoren et al, Polymer Communications, (1), 27–32, 1984. However this process has a very low selectivity and after 10 years no industrial application is known.

U.S. Pat. No. 4,322,547 describes a process which is based on the catalytic iron-copper system to obtain 9 amino nonanoic acid and azelaic acid starting from cyclohexanone and acrylonitrile. This process entails the use of amounts of catalyst, by weight, that are extremely high and indeed comparable with the weight of the product obtained. Furthermore, the copper must be introduced in the process before the iron, and therefore after mixing it is very difficult to separate the iron from the copper to recycle them; problems accordingly arise in disposing of the used and mixed catalyst. The by-products that are obtained are furthermore very difficult to separate.

Due to the above indicated reasons, after 15 years this process has had no industrial application, whereas the above described ozonolysis process is still industrially in use after more than 20 years.

The aim of the present invention is therefore to solve the problems and drawbacks of known processes, allowing to obtain highly pure products that have high selectivity so as to attain the "polymer-grade" purity required to produce polyamides 9 or 6,9 and "pharmaceutical-product grade" purity for azelaic acid.

An object is to start from industrial products of petrochemical origin that have a low cost and are widely available.

Another object is to allow to obtain a single desired final product without accessory co-productions.

This aim, these objects and others are achieved by the process according to the invention for producing an omega-functionalized aliphatic-chain carboxylic acid with more than 7 carbon atoms, which includes the following steps:

(i) the addition, in a basic environment, of the compound with formula (1)

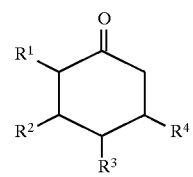

and of the compound with formula (2)

$$CH_2=CR^5 \qquad (2)$$

where each one of $R^1$, $R^2$, $R^3$, and $R^4$ is: hydrogen, alkyl, alkyl aryl, halogen, or hydroxyl; $R^5$ is Y or a group that can be transformed into Y with known methods: Y is —COOH, —CN, —CONH$_2$, or COOR$^6$; and $R^6$ is an optionally substituted alkyl or aryl radical, obtaining the compound with formula (3)

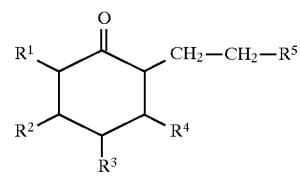

where $R^1$–$R^5$ have the above specified meaning;

(ii) the oxidation of the compound with formula (3), obtaining the compound with formula (5)

$$R^1OOC—CHR^2—CHR^3—CHR^4—(CH_2)_m—R^7—(CH_2)_n—R^5 \qquad (5)$$

where $R^1$–$R^5$ have the above specified meaning; R7 is CH=CH or CHR$^8$—CH$_2$; $R^8$ is OH, OCOCH$_3$, OCH$_3$, OEt, or halogen; m is 0, 1 or 2; n is 0 or 1; and m+n is 1 or 2;

(iii) the hydrogenation or hydrogenolysis of the compound with formula (5), obtaining an omega-functionalized aliphatic-chain carboxylic acid.

A first embodiment of the process is illustrated by way of non-limitative example in the following reaction diagram (I):

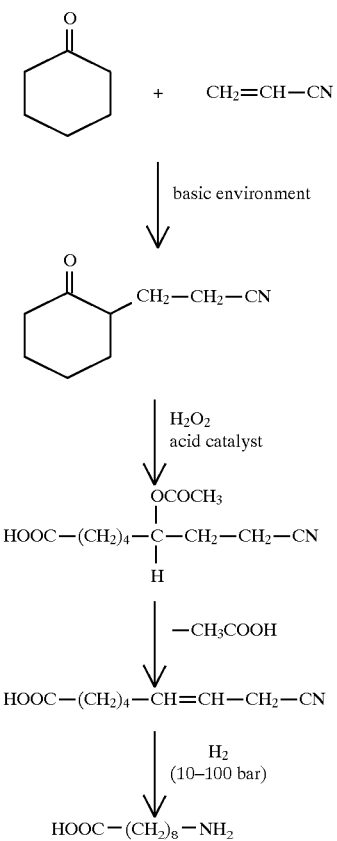

A second embodiment of the process is illustrated by way of non-limitative example in the following reaction diagram (II):

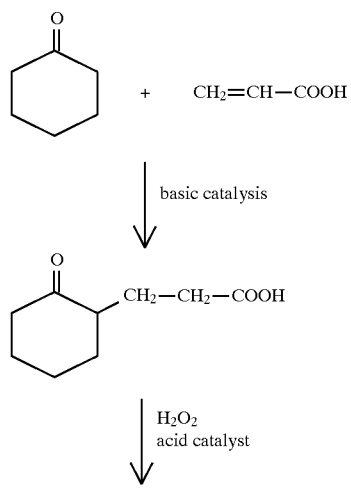

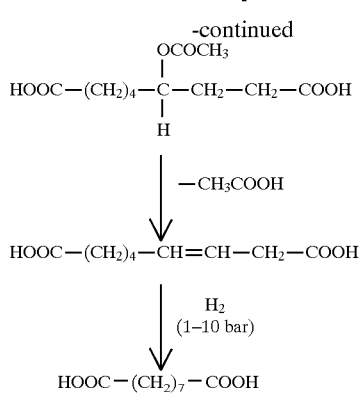

Other embodiments of the process are shown by way of non-limitative example in the following reaction diagram (III):

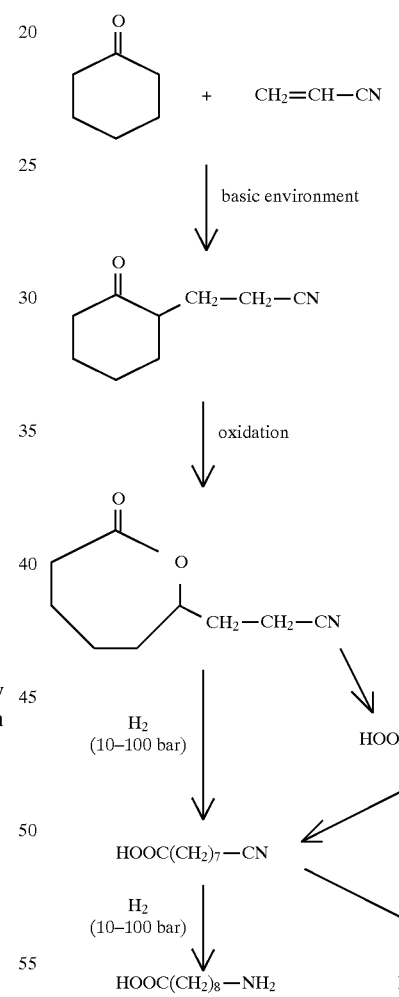

Preferably, step (i) is performed in a basic environment, more preferably in the presence of a compound chosen among ammonia, primary, secondary aliphatic and alicyclic amines, and their mixture with tertiary aliphatic and alicyclic amines. The temperature of the reaction in step (i) is preferably between 20° and 200° C., more preferably between 40° and 180° C., and more preferably between 60° and 160° C.

The compound with formula (3) can be constituted for example by: 3-(2-cyclohexanonyl)propionitrile, 3-(2- cyclohexanonyl)propionic acid, methyl 3-(2-cyclohexanonyl)propionate, butyl 3-(2-cyclohexanonyl)propionate.

According to a first embodiment, the oxidation step (ii) can be performed in the presence of an oxidizing agent chosen among hydrogen peroxide, an organic peracid and oxygen. Preferably, the organic peracid is a cycloaliphatic peracid and particularly a cyclohexane percarboxylic acid, optionally substituted in its cycloaliphatic ring. This peracid has the specific advantage that it can be obtained starting from cyclohexancarboxylic acid, which is a widely available, highly pure and low-cost product.

The oxidation step (ii) can be performed in the presence of an organic acid with less than 5 carbon atoms, preferably in the presence of a catalyst which is constituted by a strong acid, preferably methane sulfonic acid.

According to a second embodiment, the oxidation step (ii) comprises a hydrolysis step conducted in an aqueous phase in the presence of an agent chosen among NaOH, alcohol, and acetic acid. This second embodiment is particularly suitable when Y is —COOH. In this case, $R^7$ is preferably CHOH—$CH_2$, CHOCOCH$_3$—$CH_2$, CHOCH$_3$—$CH_2$, CHOEt—$CH_2$, CHhalogen—$CH_2$.

As an alternative, according to another embodiment, step (ii) is performed with molecular oxygen in the presence of a catalyst, for example a Ni catalyst complexed with 1,3-diketone or an iron oxide and an aldehyde.

The subsequent step (iii) can furthermore include dehydration or dehydrohalogenation or dealkoxylation of the compound with formula (5) to obtain the compound with formula (6)

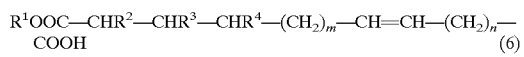

where $R^1$–$R^4$, $R^7$, m and n have the same meaning, and hydrogenation of the compound with formula (6) may also be included. This hydrogenation can be performed at a pressure between 1 and 10 bar (0.1 and 1 MPa), preferably between 2 and 5 bar (0.2 and 0.5 MPa).

If Y is —CN and $R^7$ is CH=CH, the hydrogenation step (iii) is advantageously performed at a temperature between 20° and 200° C., preferably at a temperature between 30° and 130° C., more preferably at a temperature between 40° and 70° C., and at a pressure between 1 and 200 bar (0.1 and 20 MPa), preferably at a pressure between 2 and 130 bar (0.2 to 13 MPa) to obtain an amino acid.

If $R^7$ is CH=CH, the hydrogenation step (iii) is advantageously performed at a temperature between 20° and 200° C., preferably at a temperature between 30° and 130° C., more preferably at a temperature between 40° and 70° C., and at a pressure between 1 and 200 bar (0.1 and 20 MPa), preferably at a pressure between 2 and 130 bar (0.2 and 13 MPa) and comprises basic saponification and acidification to obtain a dicarboxylic acid.

If Y is —CN and $R^7$ is CHOH—$CH_2$, CHOCOCH$_3$—$CH_2$, CHOCH$_3$—$CH_2$, CHOEt—$CH_2$, CHhalogen—$CH_2$, the hydrogenation step (iii) is advantageously performed at a temperature between 20° and 200° C., preferably at a temperature between 30° and 130° C., more preferably at a temperature between 40° and 70° C., and at a pressure between 1 and 200 bar (0.1 and 20 MPa), preferably at a pressure between 2 and 130 bar (0.2 and 13 MPa) to obtain an amino acid.

If Y is —COOH or COOR$^6$, where $R^6$ has the same meaning, and $R^7$ is CHOH—$CH_2$, CHOCOCH$_3$—$CH_2$, CHOCH$_3$—$CH_2$, CHOEt—$CH_2$, CHhalogen—$CH_2$, the hydrogenation step (iii) is advantageously performed at a temperature between 20° and 200° C., preferably at a temperature between 30° and 130° C., more preferably at a temperature between 40° and 70° C., and at a pressure between 1 and 200 bar (0.1 and 20 MPa), preferably at a pressure between 2 and 130 bar (0.2 and 13 MPa), and comprises basic saponification and acidification to obtain a dicarboxylic acid.

If $R^7$ is CHOH—$CH_2$, step (iii) can include dehydration or dehydrohalogenation or dealkoxylation of the compound with formula (5).

The invention furthermore relates to the following intermediate products that can be isolated from the reaction environment.

The compound with formula (5)

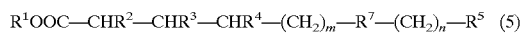

where each one of $R^1$, $R^2$, $R^3$, and $R^4$ is: hydrogen, alkyl, alkyl aryl, halogen or hydroxyl; $R^5$ is Y or a group that can be transformed into Y with known methods; Y is —COOH, —CN, —CONH$_2$, or COOR$^6$; $R^6$ is an optionally substituted alkyl or aryl radical; $R^7$ is CH=CH or CHR$^8$—$CH_2$; $R^8$ is OH, OCOCH$_3$, OCH$_3$, OEt, or halogen; m is 0, 1 or 2; n is 0 or 1; and m+n is 1 or 2. According to a preferred embodiment, the compound with formula (5) has the formula (8)

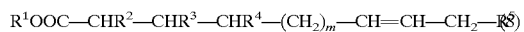

where $R^1$–$R^7$ have the same meaning and m is 0 or 1. According to an even more preferred embodiment, the compound with formula (5) has the formula (7)

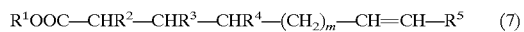

where $R^1$–$R^7$ have the same meaning and m is 1 or 2. The compounds with formulas (10) and (11) are particularly preferred:

According to another embodiment, the compound with formula (5) has the formula (9):

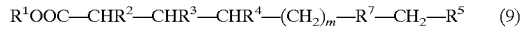

where $R^1$–$R^5$ have the same meaning; $R^7$ is CHOH—$CH_2$, CHOCOCH$_3$—$CH_2$, CHOCH$_3$—$CH_2$, CHOET—$CH_2$, CHhalogen—$CH_2$; and m is 1 or 2. Preferably, the compound with formula (5) has the formula (12):

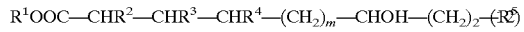

where $R^1$—$R^5$ and m have the same meaning.

The invention also relates to the compound with formula (13)

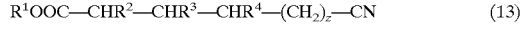

where each one of $R^1$, $R^2$, $R^3$, $R^4$ is: hydrogen, alkyl, alkyl aryl, halogen, or hydroxyl; and z is 3 or 4.

The following compounds with formulas (14) and (16) are preferred embodiments:

The following examples are enclosed by way of non-limitative example of the present invention.

EXAMPLE 1

7-cyanoethyl-2-oxepanone

A reactor is loaded with 500 g of 3-(2-cyclohexanonyl) propionitrile in 1000 ml of n-hexane; the reaction mixture is heated to 50° C. and a solution of 520 g of perhexahydrobenzoic acid in 3000 ml of n-hexane is added. The reaction mixture is kept agitated for three hours at 55° C. and then the lower phase, mainly formed by 7-cyano-ethyl-2-oxepanone and hexahydrobenzoic acid, is separated, while the upper phase contains hexahydrobenzoic acid and small amounts of unreacted cyanoketone. Treatment of the lower phase with n-hexane allows to isolate 515 g of 7-cyanoethyl-2-oxepanone, equal to a yield of over 93%, with 99% ketone conversion. The 7-cyanoethyl-2-oxepanone (m.p. 35° C.) is identified by means of I.R. (KBr) analysis techniques: 2970, 2870, 2245, 1720, 1175 cm$^{-1}$ and mass spectrometry by electron-impact ionization (70 eV): 168, 150, 139, 122, 113, 95, 84, 67, 55, 41. Analytically calculated values for $C_9H_{11}NO_2$ (167.21): C 64.65%, H 7.83%, N 8.38%. Found: C 64.51%, H 7.98%, N 8.46%.

EXAMPLE 2

7-cyanoethyl-2-oxepanone

A reactor is loaded with 151 g of 3-(2-cyclohexanonyl) propionitrile in 500 ml of n-hexane and 260 g of m-chloroperbenzoic acid (70% titer) dissolved at 50° C. in 2000 ml of n-hexane in 30 minutes. The solution is heated to 55° C. for 15 hours. Cooling of the solution separates, in crystalline form, part of the m-chlorobenzoic acid which is scarcely soluble in the system, together with a heavy liquid phase which is formed by 7-cyanoethyl-2-oxepanone and by m-chlorobenzoic acid. 71.5 g of 7-cyanoethyl-2-oxepanone, impure with m-chlorobenzoic acid, are recovered from the lower phase. 24 g of 7-cyanoethyl-2-oxepanone are recovered from the upper phase by concentration and several crystallizations. Conversion over the initial ketone is 85%. Yield on the converted amount is 57%.

EXAMPLE 3

7-cyanoethyl-2-oxepanone

A reactor is loaded with 151 g of 3-(2-cyclohexanonyl) propionitrile in 500 ml of glacial acetic acid. This solution receives the addition of 210 g of 40% peracetic acid in 2 hours, keeping the temperature between 30° and 40° C. After the addition has been completed, the reaction mixture is heated to 60° C. for 3 hours to complete the reaction. The reaction mixture is distilled in vacuum, recovering acetic acid and obtaining 150 g of an oily residue that contains 35% 7-cyanoethyl-2-oxepanone together with 65% by-products, with 98% conversion of the initial ketone (GLC analysis).

EXAMPLE 4

8-cyanoocten-7-oic acid 167 g of 7-cyanoethyl-2-oxepanone are heated in a reactor to a temperature of 450° C. in inert atmosphere, collecting 0.5 g/minute of liquid condensed product mainly formed by 8-cyano-7-octanoic acid, with 95% lactone conversion and 93% selectivity.

The product, with a b.p. of 155° C. at 0.05 torr, was identified with I.R. (film) analysis techniques: 3500, 3050, 3000, 2940, 2870, 2260, 1710, 1610, 1420, 975 cm$^{-1}$ and mass spectrometry by electron-impact ionization (70 eV): 168, 149, 121, 94, 80, 67, 55, 53, 41, 39. Analytically calculated values for $C_9H_{13}NO_2$ (167.21): C 64.65%, H 7.83%, N 8.30%. Found: C 64.55%, H 8.01%, N 8.45%.

EXAMPLE 5

8-cyanooctanoic acid 167 g of 8-cyano-7-octanoic acid dissolved in 800 ml of toluene are hydrogenated selectively at 2 bar in an autoclave in the presence of 10 g of Pd on charcoal at 5% at 50° C. for 5 hours.

After filtration of the catalyst and evaporation of the solvent, 165 g of an oil that distills at 150° C. at 0.05 torr are recovered. The product has been identified as 8-cyanooctanoic acid by I.R. (film) analysis techniques: 3400, 3000, 2950, 2875, 2260, 1710, 1430 cm$^{-1}$ and mass spectrometry by electron-impact ionization (70 eV): 170, 152, 140, 123, 110, 94, 83, 69, 55, 41. Analytically calculated values for $C_9H_{15}NO_2$ (169.22): C 63.88%, H 8.93%, N 8.28%. Found: C 63.76%, H 9.12%, N 8.37%.

EXAMPLE 6 azelaic acid 83.5 g of 8-cyanooctanoic acid dissolved in 300 ml of dimethyl ether ethylene glycol are heated to 130° C. for 4 hours in the presence of 50g of 40% caustic soda. After cooling, the reaction mixture is diluted with water, then acidified to pH 5 with diluted sulfuric acid, and then the precipitated solid is filtered. After drying, 92 g of azelaic acid with a m.p. of 107° C. are obtained.

EXAMPLE 7

9-aminononanoic acid 167 g of 8-cyano-7-octanoic acid dissolved in 1000 ml of propyl alcohol are hydrogenated at 50° C. and 80 bar for 4 hours, using 20 g of Ni-Raney as a catalyst. The catalyst is filtered out and the solution is concentrated. Cooling and purification produce 9-aminononanoic acid in the form of a crystalline solid product with a m.p. of 190°–193° C.

We claim:

1. Process for producing an omega-functionalized aliphatic-chain carboxylic acid with more than 7 carbon atoms, comprising the following steps:

(i) the addition, in a basic environment, of the compound with formula (1)

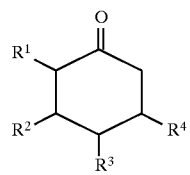

(1)

and of the compound with formula (2)

$$CH_2=CR^5 \qquad (2)$$

where each one of $R^1$, $R^2$, $R^3$, and $R^4$ is: hydrogen, alkyl, alkyl aryl, halogen, or hydroxyl; $R^5$ is Y or a group that can be transformed into Y with known methods: Y is —COOH, —CN, —CONH$_2$, or COOR$^6$; and R$^6$ is an optionally substituted alkyl or aryl radical, obtaining the compound with formula (3)

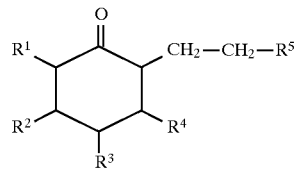

(3)

where $R^1$–$R^5$ have the above specified meaning;

(ii) the oxidation of the compound with formula (3), obtaining the compound with formula (5)

$$R^1OOC—CHR^2—CHR^3—CHR^4—(CH_2)_m—R^7—(CH_2)_n—R^5 \quad (5)$$

where $R^1$–$R^5$ have the above specified meaning; $R^7$ is CH=CH or $CHR^8$—$CH_2$; $R^8$ is OH, $OCOCH_3$, $OCH_3$, OEt, or halogen; m is 0, 1 or 2; n is 0 or 1; and m+n is 1 or 2; said oxidation being performed in the presence of an organic acid with less than five carbon atoms, preferably in the presence of a catalyst which is constituted by a strong acid;

(iii) the hydrogenation or hydrogenolysis of the compound with formula (5), obtaining an omega-functionalized aliphatic-chain carboxylic acid.

2. Process according to claim 1, wherein said step (i) is performed in a basic environment, in the presence of a compound chosen among ammonia and primary, secondary or tertiary aliphatic and alicyclic amines.

3. Process according to claim 1, wherein step (i) is performed at a temperature between 20° and 160° C.

4. Process according to claim 1, wherein said oxidation step (ii) is performed in the presence of an oxidizing agent chosen between hydrogen peroxide and an organic peracid.

5. Process according to claim 1, wherein said oxidation step (ii) is performed in the presence of a catalyst which is constituted by methane sulfonic acid.

6. Process according to claim 1, wherein Y is —COOH and said oxidation step (ii) comprises a hydrolysis step performed in an aqueous phase in the presence of an agent chosen among NAOH, alcohol, and acetic acid.

7. Process according to claim 6, wherein $R^7$ is CHOH—$CH_2$, $CHOCOCH_3$—$CH_2$, $CHOCH_3$—$CH_2$, CHOEt—$CH_2$, CHhalogen—$CH_2$, and said step (iii) comprises dehydration or dehydrohalogenation or dealkoxylation of the compound with formula (5) to obtain the compound with formula (6)

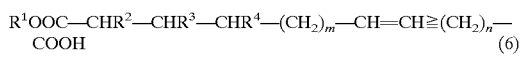
$$(6)$$

where $R^1$–$R^4$, $R^7$, m and n have the same meaning, and comprises hydrogenation of the compound with formula (6).

8. Process according to claim 7, wherein said hydrogenation is performed at a pressure between 1 and 10 bar (0.1 and 1 MPa).

9. Process according to claim 1, where Y is —CN and $R^7$ is CH=CH, said hydrogenation step (iii) is performed at a temperature between 20° and 200° C. and at a pressure between 1 and 200 bar (0.1 and 20 MPa) to obtain an amino acid.

10. Process according to claim 1, wherein $R^7$ is CH=CH, said hydrogenation step (iii) is performed at a temperature between 20° and 200° C. and at a pressure between 1 and 200 bar (0.1 and 20 MPa) and comprises basic saponification and acidification to obtain a dicarboxylic acid.

11. Process according to claim 1, wherein Y is —CN and $R^7$ is CHOH—$CH_2$, $CHOCOCH_3$—$CH_2$, $CHOCH_3$—$CH_2$, CHOEt—$CH_2$ or CHhalogen—$CH_2$, said hydrogenation step (iii) is performed at a temperature between 20° and 200° C. and at a pressure between 1 and 200 bar (0.1 and 20 MPa) to obtain and amino acid.

12. Process according to claim 1 wherein Y is —COOH or $COOR^6$, where $R^6$ has the same meaning as in claim 1, and $R^7$ is CHOH—$CH_2$, $CHOCOCH_3$—$CH_2$, $CHOCH_3$—$CH_2$, CHOEt—$CH_2$ or CHhalogen—$CH_2$, said hydrogenation step (iii) is performed at a temperature between 20° and 200° C. and at a pressure between 1 and 200 bar (0.1 and 20 MPa) and comprises basic saponification and acidification to obtain a dicarboxylic acid.

13. Process according to claim 1, wherein $R^7$ is CHOH—$CH_2$, said step (iii) comprising dehydration or dehydrohalogenation or dealkoxylation of the compound with formula (5).

14. Process according to claim 1, wherein step (i) is performed at a temperature between 40° and 140° C.

15. Process according to claim 1, wherein step (i) is performed at a temperature between 60° and 100° C.

16. Process according to claim 7, wherein said hydrogenation is performed at a pressure between 2 and 5 bar (0.2 and 0.5 MPa).

17. Process according to claim 1, where Y is —CN and $R^7$ is CH=CH, said hydrogenation step (iii) is performed at a temperature between 30° and 130° C. and at a pressure between 1 and 200 bar (0.1 and 20 MPa) to obtain an amino acid.

18. Process according to claim 1, where Y is —CN and $R^7$ is CH=CH, said hydrogenation step (iii) is performed at a temperature between 40° and 70° C. and at a pressure between 2 and 130 bar (0.2 and 13 MPa) to obtain an amino acid.

19. Process according to claim 1, wherein $R^7$ is CH=CH, said hydrogenation step (iii) is performed at a temperature between 30° and 130° C. and at a pressure between 1 and 200 bar (0.1 and 20 MPa) and comprises basic saponification and acidification to obtain a dicarboxylic acid.

20. Process according to claim 1, wherein $R^7$ is CH=CH, said hydrogenation step (iii) is performed at a temperature between 30° and 130° C. and at a pressure between 2 and 130 bar (0.2 and 13 MPa), and comprises basic saponification and acidification to obtain a dicarboxylic acid.

21. Process according to claim 1, wherein $R^7$ is CH=CH, said hydrogenation step (iii) is performed at a temperature between 40° and 70° C. and at a pressure between 2 and 130 bar (0.2 and 13 MPa), and comprises basic saponification and acidification to obtain a dicarboxylic acid.

22. Process according to claim 1, wherein Y is —CN and $R^7$ is CHOH—$CH_2$, $CHOCOCH_3$—$CH_2$, $CHOCH_3$—$CH_2$, CHOEt—$CH_2$ or CHhalogen—$CH_2$, said hydrogenation step (iii) is performed at a temperature between 20° and 200° C. and at a pressure between 2 and 130 bar (0.2 and 13 MPa) to obtain and amino acid.

23. Process according to claim 1, wherein Y is —CN and $R^7$ is CHOH—$CH_2$, $CHOCOCH_3$—$CH_2$, $CHOCH_3$—$CH_2$, CHOEt—$CH_2$ or CHhalogen—$CH_2$, said hydrogenation step (iii) is performed at a temperature between 30° and 130° C., and at a pressure between 1 and 200 bar (0.1 and 20 MPa) to obtain and amino acid.

24. Process according to claim 1, wherein Y is —CN and $R^7$ is CHOH—$CH_2$, $CHOCOCH_3$—$CH_2$, $CHOCH_3$—$CH_2$, CHOEt—$CH_2$ or CHhalogen—$CH_2$, said hydrogenation step (iii) is performed at a temperature between 40° and 70° C. and at a pressure between 1 and 200 bar (0.1 and 20 MPa) to obtain and amino acid.

25. Process according to claim 1 wherein Y is —COOH or $COOR^6$, where $R^6$ has the same meaning as in claim 1, and $R^7$ is CHOH—$CH_2$, $CHOCOCH_3$—$CH_2$, $CHOCH_3$—$CH_2$, CHOEt—$CH_2$ or CHhalogen—$CH_2$, said hydrogenation step (iii) is performed at a temperature between 20° and 200° C. and at a pressure between 2 and 130 bar (0.2 and 13 MPa) and comprises basic saponification and acidification to obtain a dicarboxylic acid.

26. Process according to claim 1 wherein Y is —COOH or $COOR^6$, where $R^6$ has the same meaning as in claim 1, and $R^7$ is CHOH—$CH_2$, $CHOCOCH_3$—$CH_2$, $CHOCH_3$—$CH_2$, CHOEt—$CH_2$ or CHhalogen—$CH_2$, said hydrogenation step (iii) is performed at a temperature between 30° and 130° C. and at a pressure between 1 and 200 bar (0.1 and 20 MPa) and comprises basic saponification and acidification to obtain a dicarboxylic acid.

27. Process according to claim 1 wherein Y is —COOH or $COOR^6$, where $R^6$ has the same meaning as in claim 1, and $R^7$ is $CHOH-CH_2$, $CHOCOCH_3-CH_2$, $CHOCH_3-CH_2$, $CHOEt-CH_2$ or $CHhalogen-CH_2$, said hydrogenation step (iii) is performed at a temperature between 40° and 70° C. and at a pressure between 2 and 130 bar (0.2 and 13 MPa) and comprise s basic saponification and acidification to obtain a dicarboxylic acid.

* * * * *